United States Patent [19]
Burrell et al.

[11] Patent Number: 5,830,724
[45] Date of Patent: Nov. 3, 1998

[54] MODIFICATION OF STARCH PRODUCTION

[75] Inventors: Michael Meyrick Burrell, Cottenham; Stephen Andrew Coates, Cherry Hinton, both of United Kingdom

[73] Assignee: Advanced Technologies (Cambridge) Limited, United Kingdom

[21] Appl. No.: 192,493

[22] Filed: Feb. 7, 1994

Related U.S. Application Data

[63] Continuation of Ser. No. 893,315, Jun. 3, 1992, Pat. No. 5,365,016.

[30] Foreign Application Priority Data

Jun. 12, 1991 [GB] United Kingdom ............... 9112645

[51] Int. Cl.$^6$ .................. C12N 15/63; C12N 15/82; A01H 5/00; C07H 21/04
[52] U.S. Cl. ................ 435/172.3; 435/69.1; 435/91.1; 435/172.1; 435/375; 435/320.1; 435/430; 47/58; 800/205; 800/250; 800/255; 800/DIG. 42; 800/DIG. 56; 800/DIG. 57; 800/DIG. 58; 536/23.2; 536/23.6; 536/24.5
[58] Field of Search .................... 800/205, 250, 800/DIG. 42, 255, DIG. 56–58; 435/172.3, 320.1, 69.1, 91.1, 375, 430; 536/24.5, 23.2, 23.6; 47/58

[56] References Cited

U.S. PATENT DOCUMENTS 5,365,016  11/1994  Burrell et al. ..................... 800/205

OTHER PUBLICATIONS

R. Visser, Doctoral Thesis, Manipulation of the Starch Composition of *Solanum Tuberosum L.* Using *Agrobacterium Rhizogenes Mediated* Transformation, 1989, Rijks Universiteit Groningen, pp. 97–109.

C. Ainsworth et al., Plant Molecular Biology, 22 ('93) 67–82.

A. Van der Krol et al., Gene, 72 ('88) 45–50.

W. James Antiviral Chemistry & Chemotherapy, vol. 2 (#4) pp. 191–214 ('91).

J.H.M. Hovenkamp–Hermelink et al., Theor. Appl. Genet., vol. 75 (1987) pp. 217–221.

R.G.F. Vissser et al, Mol. Gen. Genet., vol. 225 (1991) pp. 289–296.

R.B. Klösgen et al. Mol. Gen. Genet. vol. 203 (1986) pp. 237–244.

Z.Y. Wang et al. Nucleic Acids Research, vol. 18, No. 19 (1991) p. 5898.

J.R. Ecker et al. PNAS, vol. 83, (Aug. '86) pp. 5372–5376.

W. Schuch et al., "Modulation of Plant Gene Expression", in G.W. Lycett et al., Genetic Engineering of Crops, (London, Butterworths, 1990) pp. 221–230, ISBN 0–408–04779–8.

D. Marco et al, Potato Physiology (1985, Academic Press, Inc.) Chapter 9, pp. 279–301.

K.S. Blundy et al. Plant Mol. Biology, vol. 16 (1991) pp. 153–160.

R.B. Horsch et al. Science, vol. 223 (1984) pp. 496–498.

*Primary Examiner*—Charles C. P. Rories
*Attorney, Agent, or Firm*—Pennie & Edmonds LLP

[57] ABSTRACT

A process is provided whereby the constitution of starch produced in a plant is altered without there being a substantial change in the total amount of starch which is produced. In the process a plant cell is transformed using a chimaeric gene comprising an antisense coding sequence from the waxy locus of a plant genome or an antisense similar coding sequence from a non-plant genome.

14 Claims, 1 Drawing Sheet

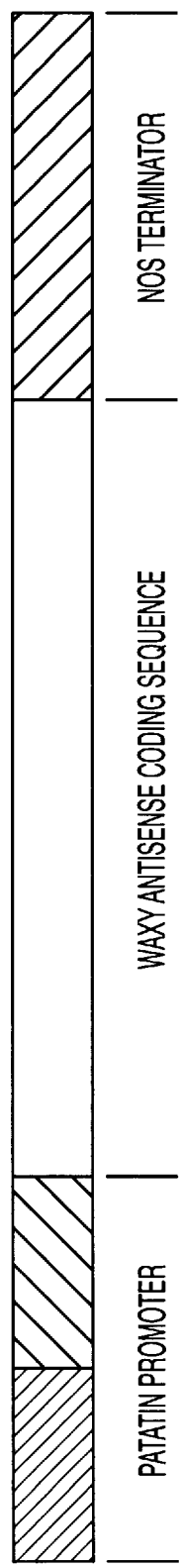

MODIFICATION OF STARCH PRODUCTION

CROSS-REFERENCE TO RELATED APPLICATION

This application is a Continuation of U.S. patent application Ser. No. 07/893,315 filed on Jun. 3, 1992 and now issued as U.S. Pat. No. 5,365,016.

BACKGROUND OF THE INVENTION

1. Field of the Invention

The subject invention relates to the process of starch production in plants.

2. Brief Description of the Related Art

It is an object of the invention to effect a change in the nature of the starch produced in a plant without reducing, or without substantially reducing, the amount of starch which the plant produces. Starch is used in the food, chemical, paper and textile industries. In these industries the nature of a starch affects its suitability for use in a particular process.

It has been reported that potato plants have been transformed to produce antisense RNA from a gene construct containing starch synthase cDNA in reverse orientation, and that this gave rise to tubers containing amylose-free starch. See "Inhibition of the expression of the gene for granule-bound starch synthase in potato by antisense constructs", R. G. F. Visser et al, Mol. Gen. Genet. (1991) 225: 289–296.

In the mutant form of maize known as waxy maize the process for producing amylose is suppressed and thereby the total amount of starch which is produced is less than is the case with maize not embodying the waxy gene.

SUMMARY OF THE INVENTION

The subject invention provides a process for altering starch production in a plant, which process comprises transforming a plant cell with a chimaeric gene comprising a promoter and an antisense coding sequence from the waxy locus of a plant genome or an antisense similar coding sequence from a non-plant genome.

BRIEF DESCRIPTION OF THE DRAWING

The drawing shows diagrammatically an anti-sense chimaeric gene used in the process of the invention.

DETAILED DESCRIPTION OF THE PREFERRED EMBODIMENTS OF THE INVENTION

The plant the subject of the inventive process is suitably a plant from which starch is commercially derived; e.g. potato, rice, wheat, barley or maize.

The genome from which the coding sequence is derived may be, for example, that of a wheat plant or a maize plant.

By "coding sequence from the waxy locus" is meant an unmutated sequence, not a sequence of or from the mutant waxy gene. The sequence can be the whole sequence or an operable part or parts thereof.

It is a result of carrying out the subject invention that the enzymic activity of starch synthase is reduced. This being the case, it would have been expected that the total amount of starch would have been reduced. Surprisingly though, there is no apparent reduction in the total amount of starch when the invention is carried into effect.

The promoter should be such as to cause the reduction in starch synthase activity to be effected at the main starch location of the plant, this being, for example, in the tubers for potato and in the seeds for wheat or rice.

An example of the inventive process will now be given.

The waxy coding sequence was obtained from a cDNA library of wheat endosperm RNA. The sequence, in sense orientation, as described by Clark et al (Plant Molecular Biology 16, 1099–1101, 1991. The waxy coding sequence was blunt end ligated into the plasmid pFW4101 in place of the GUS (B-glucuronidase) coding sequence to produce the antisense chimaeric gene (see the drawing accompanying herewith) in plasmid pFW4082. pFW4101 was constructed with a patatin promoter made from two genomic clones PS3 and PS27 as described by Blundy et al (Plant Molecular Biology 16, 153–160, 1991). The patatin fragments PS3 and PS27 were derived from the genomic clones described by Mignery et al (Gene 62, 27–44, 1988). The fragments consist of −3.5 kb to 1 kb of PS3 and −1 kb to +3 of PS27 numbered in relation to the translation start. pFW4101 was also provided with a Nos terminator sequence.

E. coli harbouring pFW4101 and Agrobacterium tumefeciens harbouring pFW4082 were deposited under the Budapest Treaty on the International Recognition of the Deposit of Micro-organisms for the Patent Procedure, at the National Collection of Industrial and Marine Bacteria, Aberdeen, GB on 5th Jul., 1990 under accession number NCIMB 40306 and on 6th Jun., 1991 under accession number NCIMB 40422 respectively.

The vector pFW4082 was transferred into Agrobacterium tumefaciens strains LBA 4404 and C58 #3 by tri parental mating. The Agrobacterium strains were used to transform the potato cultivator Desirée. A large family of over 60 transgenic plants were produced and microtubers were produced from them in vitro.

Starch synthase was assayed by making extracts of microtubers and measuring the incorporation of [$^{14}$C] from [$^{14}$C] ADPglucose into starch (methanol insoluble material) by these extracts. This assay revealed that starch synthase activity had been reduced by about 50% as compared with non-transformed plants.

To assess the starch content of the microtubers starch was first extracted from the microtubers with perchloric acid. The extracted starch was then enzymatically converted to glucose which was subsequently assayed spectophotometrically. To assess the accuracy of these measurements, control experiments were performed by taking replicate samples of the extracts to which known amounts of starch were added before starting the assay procedure.

The results showed that when starch synthase activity was reduced by 50%, the starch content of the microtubers remained constant.

In order to measure the amylose content of the starch in the transformed plants the proportion of straight chain glucan in the starch was determined by digesting the starch with exo-amylase. The glucan released was assayed spectrophotometrically and it was thereby determined that the proportion of glucan had been reduced from 60% to 30% and thus that the ratio of amylose to amylopectin was lower in the transformed plants than is the case for non-transformed plants.

As will be appreciated by those skilled in the art, whereas in the above described procedure of transforming potato,8 use was made of A. tumefaciens. In applying the subject inventive process in respect of other plants, maize, rice, wheat or barley for example, use may be made of other modes of transformation. Thus, for instance, direct transformation or electroporation may be employed.

We claim:

1. A process for increasing the amylopectin to amylose ratio in a plant, which process comprises stably transforming a plant cell selected from the group consisting of rice, wheat, barley and maize plant cells with a chimaeric gene comprising a promoter operably linked to an antisense coding sequence from the waxy locus of a wheat genome.

2. A process as claimed in claim 1, wherein a plant is regenerated from the transformed cell.

3. A process as claimed in claim 1, wherein said plant cell is a cell of a maize plant.

4. A process as claimed in claim 1, wherein said plant cell is a cell of a rice plant.

5. A process as claimed in claim 1, wherein said plant cell is a plant cell of a plant from which starch is commercially derived.

6. A transgenic plant prepared by the process of claim 1.

7. A seed of a transgenic plant, said plant having been prepared according to the process of claim 1.

8. A transgenic starch-producing plant selected from the group consisting of rice, wheat, barley and maize, said host plant having been transformed with a chimaeric gene which comprises:

(a) a promoter, (b) an antisense coding sequence from the waxy locus of a wheat genome, and (c) a terminator sequence, wherein the promoter and the terminator sequence are operably linked to the antisense coding sequence;

said transgenic plant exhibiting:

(i) reduced starch synthase activity in a seed; and (ii) no apparent reduction in the total amount of starch produced.

9. A process as claimed in claim 1 wherein said plant cell is a cell of a wheat plant.

10. A process as claimed in claim 1 wherein said plant cell is a cell of a barley plant.

11. The transgenic plant of claim 8 wherein the plant selected is rice.

12. The transgenic plant of claim 8 wherein the plant selected is wheat.

13. The transgenic plant of claim 8 wherein the plant selected is barley.

14. The transgenic plant of claim 8 wherein the plant selected is maize.

* * * * *